United States Patent
O'Brien-Coon et al.

(10) Patent No.: US 11,858,181 B2
(45) Date of Patent: Jan. 2, 2024

(54) MICROCAVITY-CONTAINING POLYMERIC MEDICAL DEVICES FOR ENHANCED ULTRASONIC ECHOGENICITY

(71) Applicant: Sonavex, Inc., Baltimore, MD (US)

(72) Inventors: Devin O'Brien-Coon, Baltimore, MD (US); David Narrow, Baltimore, MD (US)

(73) Assignee: Sonavex, Inc., Baltimore, MD (US)

( * ) Notice: Subject to any disclaimer, the term of this patent is extended or adjusted under 35 U.S.C. 154(b) by 177 days.

(21) Appl. No.: 17/192,050

(22) Filed: Mar. 4, 2021

(65) Prior Publication Data

US 2021/0331358 A1 Oct. 28, 2021

Related U.S. Application Data

(63) Continuation of application No. 16/673,542, filed on Nov. 4, 2019, now abandoned, which is a continuation of application No. 15/209,082, filed on Jul. 13, 2016, now abandoned.

(60) Provisional application No. 62/193,380, filed on Jul. 16, 2015.

(51) Int. Cl.
| | |
|---|---|
| *A61B 8/08* | (2006.01) |
| *A61B 8/14* | (2006.01) |
| *A61B 90/00* | (2016.01) |
| *B29C 44/02* | (2006.01) |
| *A61B 8/00* | (2006.01) |
| *B29L 31/00* | (2006.01) |
| *B29K 23/00* | (2006.01) |
| *B29K 105/00* | (2006.01) |
| *B29K 69/00* | (2006.01) |
| *B29C 44/04* | (2006.01) |
| *B29C 44/42* | (2006.01) |

(Continued)

(52) U.S. Cl.
CPC .............. *B29C 44/02* (2013.01); *A61B 8/587* (2013.01); *A61B 90/39* (2016.02); *A61B 8/0841* (2013.01); *A61B 8/14* (2013.01); *A61B 2090/3925* (2016.02); *B29C 44/04* (2013.01); *B29C 44/42* (2013.01); *B29K 2023/06* (2013.01); *B29K 2023/12* (2013.01); *B29K 2067/046* (2013.01); *B29K 2069/00* (2013.01); *B29K 2105/0088* (2013.01); *B29K 2105/041* (2013.01); *B29K 2995/0037* (2013.01); *B29L 2031/753* (2013.01)

(58) Field of Classification Search
CPC ............................................. A61B 2090/3925
See application file for complete search history.

(56) References Cited

U.S. PATENT DOCUMENTS

| | | | | |
|---|---|---|---|---|
| 2010/0298698 A1* | 11/2010 | Burbank | ........... | A61M 37/0069 600/431 |
| 2014/0094698 A1* | 4/2014 | Burbank | ................ | A61B 8/481 600/431 |
| 2016/0151086 A1* | 6/2016 | Field | ...................... | B29C 44/12 427/2.12 |

* cited by examiner

*Primary Examiner* — Colin T. Sakamoto
(74) *Attorney, Agent, or Firm* — Thorpe North & Western, LLP; Erik S. Ericksen

(57) ABSTRACT

An ultrasound-detectable polymeric device that offers superior visibility of the body of the device and decreased ultrasound angle dependence through the use of microcavities and methods of manufacturing thereof is disclosed. These microcavities enable superior ultrasound visualization due to diffuse reflection of sound waves when compared to solid polymeric objects, ensuring that a strong signal is received at the source of the ultrasound transducer and providing strong image contrast throughout the entire cross-section of the implant that is also robust to variable angles of insonation.

20 Claims, 2 Drawing Sheets

(51) Int. Cl.
*B29K 67/00* (2006.01)
*B29K 105/04* (2006.01)

MICROCAVITY-CONTAINING POLYMERIC MEDICAL DEVICES FOR ENHANCED ULTRASONIC ECHOGENICITY

CROSS REFERENCE TO RELATED APPLICATIONS

This application is a continuation of Ser. No. 16/673,542, filed Nov. 4, 2019, which is a continuation of U.S. application Ser. No. 15/209,082, filed Jul. 13, 2016, which claims the benefit of U.S. Provisional Application No. 62/193,380, filed Jul. 16, 2015, all of which are incorporated herein by reference in their entireties.

TECHNICAL FIELD

The presently disclosed subject matter relates generally to the design of polymeric medical devices which contain specially designed microcavities to generate improved echogenicity characteristics when visualized within the human body using ultrasound.

BACKGROUND

Noninvasive medical methods such as ultrasound imaging offer tremendous medical value and point-of-care utility for diagnosis and measurement. It often is desirable to locate a medical device which is currently within the human body or to identify a site where a procedure or measurement has been previously performed. However, interpretation of greyscale (B-mode) ultrasound requires expertise and it may be difficult to use native landmarks to determine whether the desired location has been reached. For example, returning to the site of a prior procedure can be challenging because of first, the difficulty in locating the postoperative site and second, the difficulty in determining the orientation of the image vis-à-vis earlier images collected in order to accurately analyze data collected from the location.

For the visualization of devices placed within the human body, many methods of rendering surfaces echogenic have been described. The goal of these modifications is often to make an edge (such as the edge of a metal needle) more easily visualized under ultrasound. Such methods may include machining small divots into the surface of the edge in order to reflect sonic waves in multiple directions. However, such methods are generally applicable only to metallic surfaces where the significant impedance difference between metal and human tissue means that the majority of ultrasound waves will be reflected back from the tissue-metal surface towards the transducer and will not penetrate the metallic material. For materials which are closer in acoustic impedance to human tissue, such as most polymers of medical interest, most of the ultrasound waves will pass through the polymer, generating detectable signals only at the entry and exit point of the waves. Based on our experimentation, any such surface modification attempts will fail to significantly increase the echogenicity of polymer devices. Similarly, attempts to create divots or indentations either randomly distributed across the device body or penetrating through the entire thickness of the device (e.g., from the front to back surface of the device) fail to improve echogenicity as desired.

Ultrasound tissue marker devices do exist within the medical device landscape for use in localizing sites within the body but are undesirable for certain applications because they lack such an echogenic enhancement method. These markers are often composed of a large surface area to volume ratio (e.g., they may be made up of many small pellets which may be randomly oriented) because the increased surface area maximizes the return of ultrasound waves. If the thickness of the marker body (i.e., the axis perpendicular to the beam direction) is large relative to the ultrasound wavelength, only the device edges and not the interior will be visualized. This is because substantial changes in either density or compressibility do not exist throughout the volume on a microscopic scale. For both the purposes of human visualization as well as medical imaging algorithm detection, it would often be desirable if a method were available to visualize the entire object under ultrasound rather than just the edges.

Another significant problem relates to the angle of insonation dependence with respect to the ultrasound. Devices which rely on edge-only reflectance (e.g., the previously mentioned existing markers) function as largely specular reflectors which reflect the ultrasound beam according to the standard laws of reflection. While this is desirable when the surface is perpendicular to the angle of insonation (because the strongest reflections are back towards the transducer), as the angle of insonation begins to change towards parallel most of the ultrasound energy reflects away from the transducer and is lost, making the surface dark and causing loss of the contrast necessary to visualize the object.

Therefore, what is desired is a method of producing polymer-comprised medical devices which are 1) visualized throughout their entire thickness rather than just their edges as well as 2) more tolerant of variable insonation angles while still producing echogenic contrast compared to surrounding tissue.

SUMMARY

The presently disclosed subject matter provides an ultrasound-detectable polymeric medical device with superior visibility of the body of the device and less ultrasound angle dependence. These desirable characteristics are created by introducing controlled microcavities within the marker to alter the reflection mechanism of the ultrasound waves as they pass through the implant.

The cavities have two main purposes: (a) creating differences in density and compressibility within the marker on a small scale, and (b) creating diffuse reflection robust to insonation angle as compared to what is otherwise largely specular reflection. The small-scale density changes ensure that acoustic signal reflections occur throughout the depth of penetration. The distance over which these changes occur is tuned to be relative to the wavelength of the ultrasound, with optimal cavity-polymer transitions occurring at distances comparable to the ultrasound wavelength. The proper choice of microcavity ratio and dimension is essential because creation of excessive acoustic impedance will cause premature absorption of all the ultrasound energy and failure of the object to fully illuminate, while inadequate impedance will result in the internal structure being inadequately echogenic.

However, production of density changes alone simply create greater reflections in the body of the object. For example, production of the object using an additive manufacturing process such as 3D printing yields objects with a series of layers which may cause impedance changes. However, such methods result in impedance changes that continue to be specular reflectors and result in objects seen best when perpendicular to the source of the sound wave. This renders it impossible to ever fully visualize a 3-dimensional shape where some surfaces are not perpendicular to the ultrasound beam (for example, the sides of a sphere will not show up well).

In order to accommodate various orientations of geometric shape that may be desired in, for example, an ultrasound marker device, the microcavities and their essentially random surface orientation vis-à-vis the ultrasound beam will reflect the signal in a diffuse manner. Thus the acoustic signal from the object returns to the probe irrespective of orientation and causes the whole cross-section of the object to appear visible on the ultrasound screen.

In other aspects, the presently disclosed subject matter provides a method for inserting and visualizing a medical device containing microcavities, the method comprising: (a) inserting a polymeric medical device with microcavities into a patient; (b) visualizing and detecting the device using B-mode ultrasound during or after surgery; and (c) performing this visualization in multiple near-simultaneous frames, representing different angles of insonation.

This method of detecting the medical device from multiple angles of insonation is of particular importance. In many clinical environments, it is desirable to understand the orientation of the imaging plane to gather repeatable data longitudinally, but also to assess a specific site from a variety of perspectives. Furthermore, it is rare that the user will approach the site from the proper angle, so the device must tolerate and accommodate initial error. Thus, the user of the ultrasound must be able to detect the device from essentially all angles of insonation.

BRIEF DESCRIPTION OF THE DRAWINGS

FIG. 2 displays the reflectance of the ultrasound beam for a medical device both with and without microcavities.

DETAILED DESCRIPTION

Figure 1:
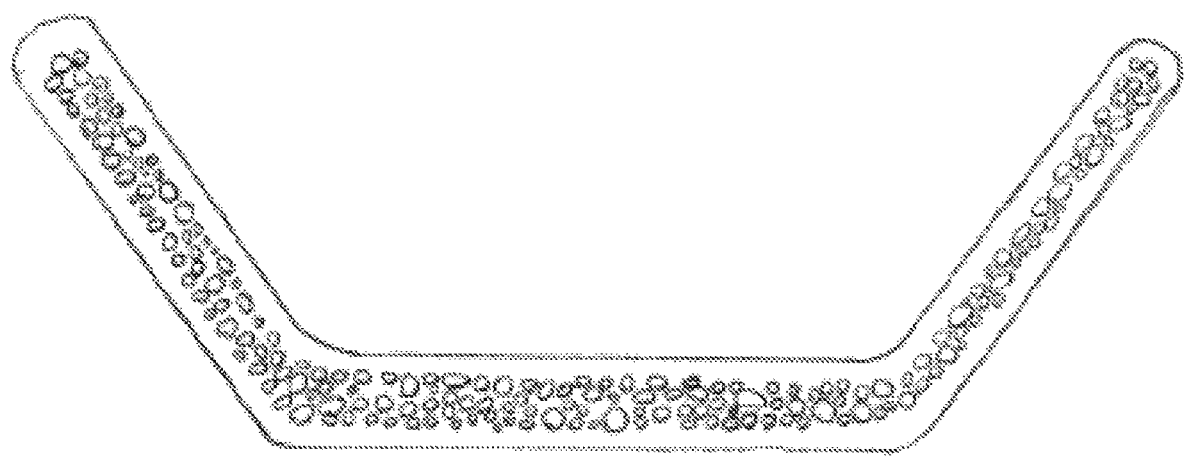
FIG. 1 displays the cross section of a medical device with internal microcavities. The cavities resemble a spherical or semi-spherical shape across a range of sizes. The device contains an outer layer free of microcavities.
Figure 2A:
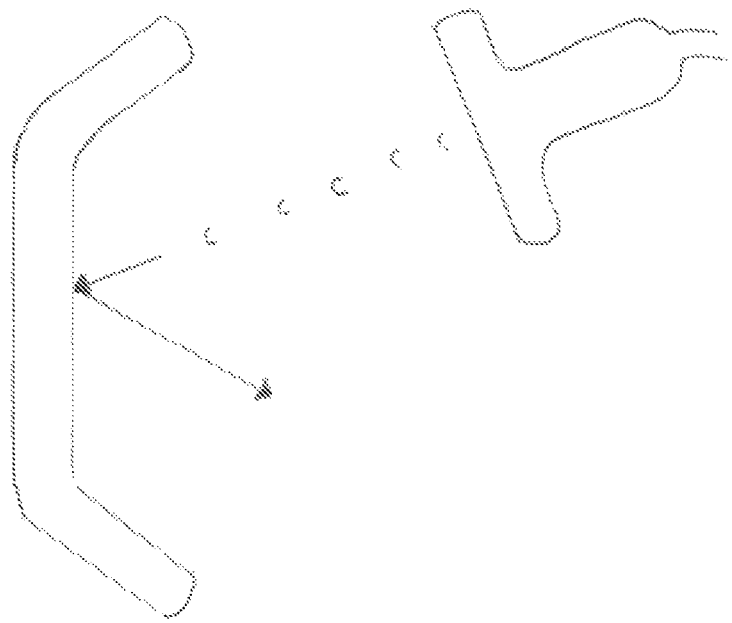
FIG. 2A, a medical device without microcavity, exhibits a specular reflection of the ultrasound beam, which results in little to no signal returning to the probe.
Figure 2B:
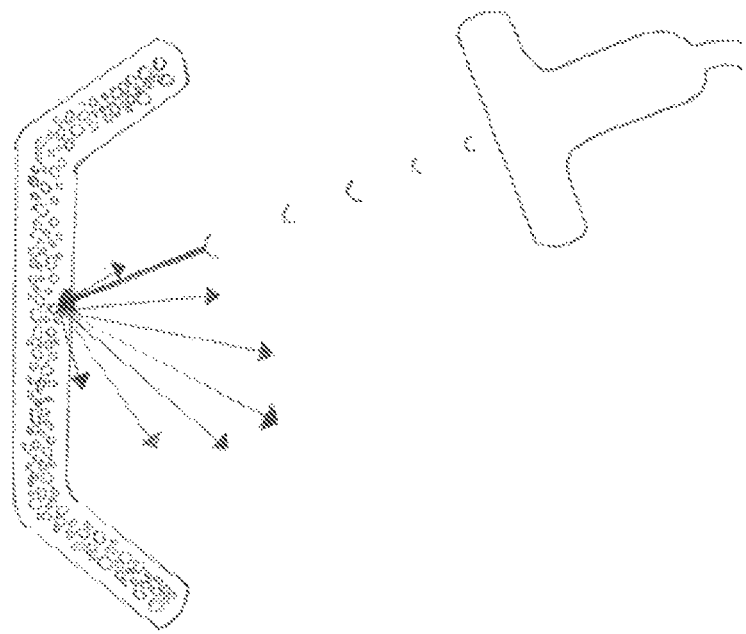
FIG. 2B displays the diffuse reflection that is generated when the ultrasound beam contacts the microcavities. Unlike in FIG. 2A, a significant portion of the signal is reflected back to the probe, irrespective of the originating angle of the emitted signal.

In one aspect, the invention provides an ultrasound-detectable medical device comprising a polymer with microcavities dispersed in some or all of its body capable of providing improved visibility throughout some or all of its volume and under variable angles of insonation FIGS. 1 and 2B. In some instances, the microcavities extend throughout the entire volume of the medical device. In other instances, the microcavities occupy a central region of the medical device. In additional instances, the space containing microcavities is surrounded by an outer layer of material without microcavities.

In another aspect, the invention provides an ultrasound-detectable device wherein the diameter (microcavity size) ranges between 0.1 to 950 microns, and commonly between 50 to 350 microns. In some instances, the microcavity diameter exceeds 1,000 microns. In other instances, the microcavity diameter ranges from 10 to 500 microns. In additional instances, the microcavities exhibit diameters from 10 to 1,500 microns.

In a further aspect, the invention provides an ultrasound-detectable device wherein the ideal volume to volume ratio of cavity space to polymer structures should be less than 60%, and is commonly between 12% and 50%. In some instances, the microcavities comprise between 30 to 50% of the volume. In other instances, the volume ratio of microcavities exceeds 60%.

The ultrasound-detectable device contains microcavities. In one aspect of the device, the microcavities are composed of gas. In one aspect of the invention, the device is created via injection molding. In another embodiment, the device is manufactured by extrusion. In some aspects of the invention, microcavities are created by introducing gas into the polymer material prior to manufacturing, commonly through injection. In other aspects of the invention, microcavities are introduced during the manufacturing process, which can be performed by injecting gas into a mold either before, while, or after the polymer enters the mold.

The microcavities may be composed of a variety of biocompatible gases. In some instances, super-critical $CO_2$ is used, and in other instances, $N_2$ is used.

In another embodiment, the microcavities are created via a chemical reaction such that gas is released into the polymer. This may be accomplished with a foaming agent or other chemical processes. The gas may be activated by pressure or temperature changes in the manufacturing process.

For a variety of reasons, including mechanical, material degradation, visibility, and manufacturing considerations, it is desirable to have the microcavities consume a region within the overall volume, rather than the entire device. In one embodiment, the region containing the microcavities is central to the device. In this embodiment, the region containing the microcavities is surrounded by a layer of polymeric or non-polymeric material that does not contain microcavities. In other embodiments of the device, this external layer, or "skin", contains microcavities, though of a reduced density. In further embodiments, the region containing the microcavities resides on the top surface of the device (superficial towards the position of the ultrasound probe), while in other embodiments, the microcavity region resides on the bottom surface of the device.

In one aspect of the invention, there is an outer layer of the device which is meant to maintain the structural integrity of the inner microcavity-containing region. This outer layer does not contain microcavities and thus provides a barrier protecting the inner region, especially from fluid flow, which could accelerate degradation and also negatively impact the ultrasonic visibility. In another aspect of the invention, the outer layer described has a smooth surface to minimize irritation and other adverse events to surrounding tissue or vessels once the device is implanted.

Another aspect of the device relates to the visibility of the device under ultrasonic imaging. In this aspect, the device is used as an echogenic marker for ultrasound location in the human body. Some anatomic structures that can be marked using this device include: veins, arteries, soft tissue, urinary tracts, nerves, and ducts. The device enables location of any of these structures after implantation. In particular, the device gives the clinician knowledge of the spatial relationship between the ultrasound probe and anatomic structure, independent of the angle of insonation. The device enables locating the anatomic location repeatedly across many examinations after placement of the device. The size of the device ranges from 1 to 60 mm in length, 1 to 60 mm in width, and 1 to 40 mm in height. Some embodiments of the device represent curved, cradle-like structures. Other embodiments of the device are spheres, rectangles, cubes, plates, pellets, and discs. Some instances of when this device could be used are for: microvascular anastomoses, solid organ transplants, vascular bypass, and vascular access.

In one embodiment of the device, it is comprised of one or more resorbable polymers selected from the group of: poly(lactic-co-glycolic acid) (PLGA), polylactide (PLA), polyglycolide (PGA), polyhydroxyalkanoate (PHA), polycaprolactone (PCL), polyethylene glycol (PEG) and copolymers thereof.

In another embodiment of the device, it is comprised of one or more non-resorbable polymers selected from the group of: polycarbonate, polyetheretherketone, polypropylene, silicone, polyethylene, polyester, polybutylene terephthalate (PBT), polyvinyl chloride, polyethylsulfone, polyacrylate, polyetheretherketone, poly-p-xylylene (parylene), polytetrafluoroethylene, cyclo olefin, acrylonitrile butadiene styrene, polyeurethane, acrylonitrile styrene acrylate, acetals, polyetherimide, ethylene, chlorotrifluoroethylene, ethylene tetrafluoroethylene, polyvinyl fluoride, polyvinylidene difluoride, and polyhydroxybutyrate. In a further embodiment, the device is comprised of both resorbable and non-resorbable materials, which may be in the form of multiple sections with unique materials, a single blend of materials, or multiple sections of blended materials.

In one aspect of the invention, the device is manufactured via a foaming process. Microcavities are introduced into the polymer by introducing a blowing agent. The blowing agent created the cellular structure of the microcavities. In one embodiment of the invention, the blowing agent is a physical blowing agent. In another embodiment, the blowing agent is a chemical blowing agent. An alternative way of generating the foam is using a solvent such as acetone. In addition to introducing the foaming agent, this invention describes injecting the polymer into a mold. An alternative way of producing the device is via extrusion.

This invention describes a method for using the device where the device is first inserted into a patient, it is then detected using B-mode ultrasound during or after surgery, and the device is detected in multiple frames, representing different angles of insonation. The ultrasound user can leave the patient and return to find the device at a later time point. This is important because it is often desired to track anatomical or physiological features over a time horizon of multiple days or weeks, and sometimes months or years. This means that user needs to walk away from the patient, return to the patient, and easily locate the device. Another critical feature of the invention is the ability to detect the device using ultrasound from any angle of insonation. This is important because a non-expert is able to locate the marked site and use the visual information to achieve a desired angle or set of angles. The invention enables strong visibility in angles ranging from 25 degrees to 155 degrees from the skin surface. The microcavity feature of the invention provides the ability to visualize the device across such a broad range of insonation angles. Due to the geometry and microcavity feature of the device, the user is able to understand the angle of insonation. Therefore, the user can repeatedly match the same orientation upon each examination, generate the same image of the device, and thus compare anatomic or physiologic conditions reliably over time. Alternatively, the user can approach the device from a new orientation in each additional examination, though will have the geometric information from the device to make proper calculations to adjust for the new angle of insonation.

The device should not be compromised at 40 degrees Celsius when in a dark and moist environment, such as human or animal tissue. Compromise includes but is not limited to geometric changes, mechanical deformation, degradation, or microcavity change. The device must maintain its original integrity for at least 72 hours in such conditions. The device must yield contrast when visualized using B-mode ultrasound between 1 cm and 5 cm deep from the surface of the skin.

Examples

Example 1. An ultrasound-detectable medical device made by extrusion. Specifically, a Nano 16 mm extruder was used with a GFA3-10-30 screw element at 270 mm. The extruder has four zones, each with individual temperature control, which ultimately lead to a die to achieve the desired geometry of the device. The zones were first preheated to 110, 140, 130 and 100° C. respectively. The pressure within the die ranged from 10-70 psi. The feeding rate of the polymer was 2.5 cc/min, and the screw speed fell between 75-100 rpm. The torque on the screw ranged from 1500-3000 Gm. The supercritical CO2 was injected at 200 psi with a flow rate of 20 cfh. When the extruded polymer left the die, it was cooled via an air jacket. In cases when it was desired to achieve variance along the extrusion axis, the device was laser cut once it cooled to room temperature using the air jacket.

Example 2. An ultrasound-detectable medical device made by injection molding. The polymer was introduced into the mold via injection through the port. While the material was being injected into the mold, $CO_2$ gas was simultaneously injected to provide microbubbles. In another example, the $CO_2$ was introduced into the material prior to injection into the mold. Once the material filled the mold, the mold was released via its pins, the part was removed, and the process was repeated.

We claim:

1. An ultrasound-detectable device comprising:
   a polymer material including a first region and a second region, the first region continuously enveloping the second region over an entirety of a surface area of the device; and
   a plurality of microcavities dispersed within the second region and configured to reflect ultrasonic signals transmitted at one or more angles toward the device when the device is implanted in a patient.

2. The ultrasound-detectable device of claim 1, wherein a diameter of at least one microcavity of the plurality of microcavities is between 0.1 and 950 microns.

3. The ultrasound-detectable device of claim 1, wherein a diameter of at least one microcavity of the plurality of microcavities is between 50 and 350 microns.

4. The ultrasound-detectable device of claim 1, wherein the plurality of microcavities occupy less than 60% of a total volume of the device.

5. The ultrasound-detectable device of claim 1, wherein the plurality of microcavities occupy between 12% and 50% of a total volume of the device.

6. The ultrasound-detectable device of claim 1, wherein the microcavities include at least one gas.

7. The ultrasound-detectable device of claim 6, wherein the at least one gas is selected from $CO_2$ or $N_2$.

8. The ultrasound-detectable device of claim 1, wherein the blowing agent is a chemical blowing agent.

9. The ultrasound-detectable device of claim 1, wherein the device provides improved visibility throughout a volume of the device under varying angles of insonation as compared to a similar device without microcavities.

10. The ultrasound-detectable device of claim 1, wherein the first region includes a non-porous layer of polymer material devoid of microcavities, the non-porous layer forming a barrier with respect to the second region.

11. The ultrasound-detectable device of claim 1, wherein the device is an echogenic marker to receive ultrasonic signals transmitted into the human body by an ultrasonic probe and to reflect the transmitted ultrasonic signals back to the ultrasonic probe.

12. The ultrasound-detectable device of claim 1, wherein the polymer material comprises one or more resorbable polymers selected from the group consisting of poly(lactic-co-glycolic acid) (PLGA), polylactide (PLA), polyglycolide (PGA), polyhydroxyalkanoate (PHA), polycaprolactone (PCL) and copolymers thereof.

13. The ultrasound-detectable device of claim 1, wherein the polymer material comprises one or more non-resorbable polymers selected from the group consisting of polyurethane, polycarbonate, polyetheretherketone, polypropylene, silicone, polyethylene, polyester, polybutylene terephthalate (PBT), polyvinyl chloride, polyethylsulfone, polyacryclate, poly-p-xylylene (parylene), polytetrafluoroethylene, cyclo olefin, acrylonitrile butadiene styrene, acrylonitrile styrene acrylate, acetals, polyetherimide, ethylene, chlorotrifluoroethylene, ethylene tetrafluoroethylene, polyvinyl fluoride, polyvinylidene difluoride, and polyhydroxybutyrate.

14. The ultrasound-detectable device of claim 1, wherein a shape of the device includes a cradle-shape, a spherical-shape, a rectangular-shape, a cube-shape, a disc-shape, or a cylindrical-shape.

15. The ultrasound-detectable device of claim 1, wherein the first region includes microcavities dispersed at a reduced density compared to a density of the microcavities in the second region.

16. The ultrasound-detectable device of claim 1, wherein the plurality of microcavities are formed by foaming the polymer material via a blowing agent injected into the polymer material.

17. A method of use comprising:
providing an echogenic marker including a polymer material including a first region and a second region, the first region continuously enveloping the second region over an entirety of a surface area of the echogenic marker, the echogenic marker includes a plurality of microcavities dispersed within the second region that are configured to reflect ultrasonic signals transmitted at one or more angles toward the echogenic marker when the echogenic marker is implanted in a patient, wherein the plurality of microcavities are formed by foaming the polymer material via a blowing agent injected into the polymer material;
inserting the echogenic marker in a patient;
detecting the echogenic marker using B-mode ultrasound during or after surgery based on ultrasonic signals reflected by the plurality of microcavities dispersed within the second region; and
detecting the echogenic marker in a frame associated with a reflected ultrasonic signal, the frame corresponding to a unique angle of insonation of an ultrasonic signal transmitted toward the echogenic marker during or after surgery.

18. The method of claim 17, wherein the unique angle of insonation is between 25 and 155 degrees relative to a surface of skin of the patient.

19. The method of claim 17, wherein the microcavities are created via a chemical reaction within the polymer material such that a gas is released, the gas activated by a change in a temperature or a pressure applied during manufacture of the device.

20. A method of manufacture comprising:
forming an echogenic marker by injecting a polymer material into a mold, the echogenic marker including a plurality of microcavities, a first region devoid of microcavities, and a second region including the plurality of microcavities dispersed within the second region, the first region continuously enveloping the second region over an entirety of a surface area of the echogenic marker, wherein the plurality of microcavities are formed by injecting a blowing agent into the polymer material and reflect ultrasonic signals transmitted at one or more angles toward the echogenic marker when the echogenic marker is implanted in a patient.

* * * * *